United States Patent [19]
Grenouillet

[11] Patent Number: 5,373,856
[45] Date of Patent: Dec. 20, 1994

[54] CATHETER GUIDE FORMED NOTABLY FROM A MULTISTRAND SPRING SHEATH

[75] Inventor: Guy Grenouillet, Villers-Le-Lac, France

[73] Assignee: Nivarox-FAR S.A., Le Locle, Switzerland

[21] Appl. No.: 120,464

[22] Filed: Sep. 14, 1993

[30] Foreign Application Priority Data

Sep. 29, 1992 [FR] France ............... 92 11733

[51] Int. Cl.⁵ .................................. A61B 5/00
[52] U.S. Cl. ...................................... 128/772
[58] Field of Search ........... 128/657, 658, 772; 604/95, 280–283

[56] References Cited

U.S. PATENT DOCUMENTS

| | | | |
|---|---|---|---|
| 4,003,369 | 1/1977 | Heilman et al. | |
| 4,020,829 | 5/1977 | Willson et al. | 128/772 |
| 4,721,117 | 1/1988 | Mar et al. | 128/772 |
| 5,241,970 | 9/1993 | Johlin et al. | 128/772 |

FOREIGN PATENT DOCUMENTS 145489  6/1985  European Pat. Off. .
247371 12/1987  European Pat. Off. .

*Primary Examiner*—Max Hindenburg
*Attorney, Agent, or Firm*—Sughrue, Mion, Zinn, Macpeak & Seas

[57] ABSTRACT

The invention concerns a catheter guide (1) comprising a wire (2) having a proximal part (6) of approximately constant cross section and a tapered distal part (8) and a supple protective sheath (4) formed by a helicoidal spring extended at least around the length of the tapered distal part (8) the wire (2) being fixed to the sheath (4) by at least the free end of its proximal part by means of a first solder joint (10) at a proximal part (12) of the sheath, the free end (14) of the distal part of the sheath (4) being provided with a second solder joint (16) forming a rounded end, wherein the spring forming the sheath comprises, along its entire length, a first strand (18) wound with a first pitch for forming a series of first windings S18 and at least a second strand (20,22,24) wound with a second pitch of a value slightly greater than that of the first pitch for forming a series of second windings (S20,S22,S24) such that the first windings (S18) exert a compressive force on the second windings (S20, S22, S24).

3 Claims, 1 Drawing Sheet

CATHETER GUIDE FORMED NOTABLY FROM A MULTISTRAND SPRING SHEATH

BACKGROUND OF THE INVENTION

The invention concerns guides in general and more particularly a guide formed from a multistrand spring sheath intended to be introduced into a blood-vessel of narrow diameter so as to allow the introduction of a catheter.

This type of sheath has many applications, notably in the field of cardiovascular surgery such as, for example, during a coronary angioplasty during which a catheter is introduced into a narrow region of the coronary artery of the patient and is inflated to dilate this narrow region.

From the document U.S. Pat. No. 4,548,206 a catheter guide is known which is intended to be introduced by an intravascular path into the human body.

According to this document, the guide comprises a wire or mandril having a proximal part of constant diameter and a tapered distal region. A sheath, formed from a monostrand helicoidal spring having an interior diameter approximately equal to the diameter of the proximal part of the wire, is threaded onto the wire. The proximal extremity of the wire is fixed to the proximal extremity of the spring by a brazed joint and the distal extremity of the wire is left free in the distal region of the spring. Finally, the guide comprises a safety wire formed by a narrow wire which passes along the length of the spring through its interior, and which is also fixed at its two extremities by a brazed joint. The function of the safety wire is to maintain the cohesion of the spring windings and avoid its dislocation when it is submitted to traction.

However, taking into account the very small diameter of these guides, in the order of 0.5 mm, and its relatively important length (as long as 2 m), these guides have a great flexibility which makes them fragile and delicate to manipulate, store and transport.

In fact, it has been observed that during the manipulation and transportation of these sheaths, a great number of them have undergone deformations and notably the dislocation of the windings, which results in them being unsuitable for use.

In fact, such a dislocation forms an extra thickness which reduces or even blocks the sliding of the catheter in the guide.

Furthermore, the need to prepare the safety wire, which must be successively drawn to a convenient diameter in order to then be covered, dressed, cut to length, fettled, and then washed, before being introduced manually in the sheaths and soldered, makes the fabrication costly and time consuming.

It should also be noted that the cross section of the safety wire is very small ($1,4 \times 10^{-2}$ mm) and that the resistance of its fastenings is weak. It can thus easily be seen that an incorrect manipulation of the guide can easily lead to traction on the safety wire, resulting in its rupture. Such a rupture can cause the unwinding of the spring which, if occurring in a vein of a patient, can cause serious complications notably during its extraction.

SUMMARY OF THE INVENTION

The invention has therefore as its principal aim to remedy the inconveniences of the above-mentioned prior art by providing a guide having an improved reliability and for which the fabrication is simple and inexpensive.

In this regard the object of the invention is a catheter guide comprising a wire having a proximal part of approximately constant cross-section and a tapered distal part, and a supple protective sheath formed by a helicoidal spring passing at least around the length of the tapered distal part, the wire being fixed to the sheath by at least the free extremity of its proximal part by means of a first solder joint in a proximal part of the sheath, the free extremity of the distal part of the sheath being provided with a second solder joint forming a rounded extremity, characterised in that the spring forming the sheath comprises, along its entire length, a first strand wound with a first pitch for forming a series of first windings and at least a second strand wound with a second pitch of a slightly greater value than that of the first pitch for forming a series of second windings, such that the first windings exert a compressive force on the second windings.

Thus, the cohesion of the spring windings is increased. The cohesion of the windings thus reinforced, the risk of dislocation of the windings is diminished and the safety wire and its accompanying inconveniences may be dispensed with.

According to an advantageous feature of the invention, the spring may comprise four strands.

The use of four strands has proved to constitute a good compromise, taking into account the complexity of the machines used to realize the sheath, the cohesion of the windings obtained and the rolling time of the sheaths which is reduced with respect to the time necessary to realize a sheath comprising a single strand spring.

BRIEF DESCRIPTION OF THE DRAWINGS

Other characteristics and advantages of the invention will appear more clearly from the reading of the following description of a purely illustrative and non-limitative embodiment of a guide according to the invention, this description being made in combination with FIG. 1 representing a partial section of an embodiment of the guide according to the invention.

DESCRIPTION OF A PREFERRED EMBODIMENT

Figure 1:
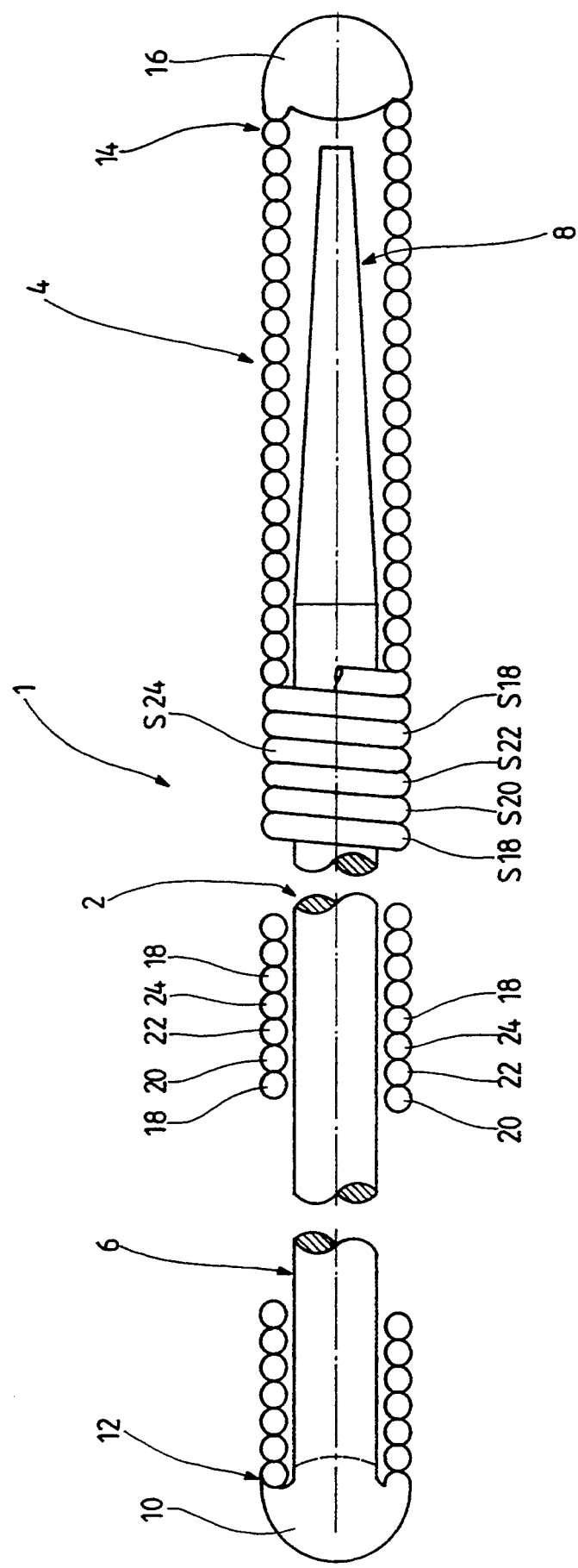

Referring to FIG. 1, a catheter guide according to the invention is seen which is designated by the general reference 1. Such a guide may be used in surgery in the performance of angioplasty procedures, notably for permitting the introduction and positioning of a catheter such as an exploratory catheter for treatment or similar use in the cardiovascular system of a patient.

For the introduction of the catheter it is therefore necessary to introduce, firstly, the guide to the zone of treatment of the cardiovascular system and, secondly, to slide the catheter into the treatment zone.

As can be seen clearly from FIG. 1, the guide 1 comprises a wire 2, or mandril, forming the heart of the guide, onto which is threaded a protective sheath 4 fixed to this wire.

The wire 2, preferably of stainless steel, comprises a proximal part 6 of approximately constant cross-section and a tapered distal part 8.

The proximal part 6 has a generally cylindrical form and the distal part 8 has a form in the shape of a conconic cone. It will be noted in this regard that the distal part 8 can have any other form according to, for example, the degree of suppleness required for the application in which the guide 1 is to used.

As an example only, the diameter of the part 6 of constant cross section of the wire 2 is in the order of 0,3 mm and the diameter of the extremity of the distal part of the wire 2 is of the order of 0,1 mm.

The protective sheath 4 is formed by a helicoidal spring having contiguous windings. In the example of the guide 1 represented, the sheath 4 extends around the wire 2 and over its entire length. It will be equally noted that the interior diameter of the sheath 4 is approximately equal to the diameter of the proximal part 6 of the wire 2.

The sheath 4 is fixed to the wire 2 by means of a first solder joint 10 which connects its first extremity 12, situated at its proximal part, to the free end of the proximal part 6 of the wire 2. The second free extremity 14 of the sheath 4 is provided with a second solder joint 16 which forms a rounded end of which the diameter is preferably approximately equal to that of the sheath 4. Thus, due to the rounded form and the dimensions of this solder joint 16, the risk of lesion of the internal wall of a vein during the introduction therein of the guide 1 is greatly reduced and this introduction is also more easily performed.

As to the distal extremity 8 of the wire 2, this is free at a certain distance from the second extremity 14 of the sheath. This distance can, of course, vary depending upon the suppleness of the desired use for the end of the guide 1. In another embodiment, the distal extremity 8 of the wire 2 could be fixed to the solder joint 16.

It will be noted that the solder joints are advantageously made without the addition of further material.

According to the invention, the spring forming the sheath 4 comprises a first strand 18 wound with a first pitch P1 for forming a series of first windings S18 and three other strands 20, 22 and 24 wound respectively with a second pitch P2 of a value slightly greated than that of the first pitch P1 to form three series of second windings S20, S22 and S24. The pitch is of course defined by the distance between two successive windings formed by the same strand when that strand is in a free state. Thus, if the windings S22, S24 and S26 were free, they would have a pitch P2 greater than that of the winding S22 such that the winding S20 compresses the others and maintain a cohesion between the windings.

By winding the first strand and the other strands respectively with a first pitch P1 and a second pitch P2, it will be understood that the machine which winds the first and the three other strands is controlled in a appropriate manner to form the first strand and the three other strands with the pitches P1 and P2.

Thanks to this structure, the successive windings S22, S24 and S26 respectively of the three other strands 22, 24 and 26 are maintained in a regularly compressed state by two successive windings S20 of the first strand 20 so that the stiffness of the spring forming the sheath 4 is increased and the cohesion of its windings improved.

Of course the result of winding the multistrand spring forming the sheath leads to the fabrication of a spring having joined windings, the pitches P1 and P2 representing imaginary pitches because all the windings of the spring are joined.

What is claimed is:

1. Catheter guide comprising a wire having a proximal part of approximately constant cross section and a tapered distal part and a supple protective sheath formed by a helicoidal spring extended at least around the length of the tapered distal part the wire being fixed to the sheath by at least the free end of its proximal part by means of a first solder joint at a proximal part of the sheath, the free end of the distal part of the sheath being provided with a second solder joint forming a rounded end, wherein the spring forming the sheath comprises, wound along the entire length of the guide a first strand wound with a first pitch for forming a series of first windings; and at least a second strand wound with a second pitch of a value slightly greater than that of the first pitch for forming a series of second windings such that the first windings exert a compressive force on the second windings.

2. Catheter guide according to claim 1, wherein in that the spring comprises four strands.

3. The catheter guide, according to claim 1, having a diameter on the order of 0.5 mm and a length up to and including two meters.

* * * * *